United States Patent
Raaijmakers et al.

(10) Patent No.: US 6,447,770 B1
(45) Date of Patent: Sep. 10, 2002

(54) BIOCONTROL AGENTS FOR TAKE-ALL

(75) Inventors: Jos M. Raaijmakers; David M. Weller; Linda S. Thomashow; R. James Cook, all of Pullman, WA (US)

(73) Assignee: The United States of America as represented by the Secretary of Agriculture, Washington, DC (US)

(*) Notice: Subject to any disclaimer, the term of this patent is extended or adjusted under 35 U.S.C. 154(b) by 0 days.

(21) Appl. No.: 09/395,861

(22) Filed: Sep. 14, 1999

Related U.S. Application Data

(63) Continuation of application No. 08/974,938, filed on Nov. 20, 1997, now abandoned.

(51) Int. Cl.$^7$ .......................... A01N 63/00; C12N 1/20; C12N 1/00
(52) U.S. Cl. ............................. 424/93.47; 435/252.34; 435/253.3; 435/876
(58) Field of Search .................. 435/252.34, 253.3, 435/876; 424/93.47

(56) References Cited

U.S. PATENT DOCUMENTS 4,456,684 A  6/1984  Weller et al. ................. 435/34

OTHER PUBLICATIONS

M.G. Bangera, D.M. Weller, and L. S. Thomashow, "Genetic Analysis of the 2,4–Diacetylphloroglucinol Biosynthetic Locus from *Pseudomonas Fluorescens* Q2–87," In: *Advances in Molecular Genetics of Plant–Microbe Interactions*, vol. 3, (Eds) M.J. Daniels, J.A. Downie, and A.E. Osbourn, Kluwer Academic Publishers, Dordrecht, pp. 383–386 (1994).

R.F. Bonsall, D.M. Weller, and L.S. Thomashow, "Quantification of 2,4Diacetylphloroglucinol Produced by Fluorescent *Pseudomonas* spp. In Vitro and in the Rhizosphere of Wheat," *Applied and Environmental Microbiology* 63:951–955 (Mar. 1997).

R.J. Cook, L.S. Thomashow, D.M. Weller, D. Fujimoto, M. Mazzola, G. Bangera, and D.S. Kim, "Molecular Mechanisms of Defense by Rhizobacteria against Root Disease," *Proc. Natl. Acad. Sci. U.S.A.* 92:4197–4201 (1995).

C. Keel, D.M. Weller, A. Natsch, G. Defago, R.J. Cook and L.S. Thomashow, "Conservation of the 2,4–Diacetylphloroglucinol Biosynthesis Locus among Fluorescent Pseudomonas Strains from Diverse Geographic Locations," *Applied and Environmental Microbiology* 62:552–563 (1996).

M. Mazzola, D.K. Fujimoto, L.S. Thomashow, and R.J. Cook, "Variation in Sensitivity of *Gaeumannomyces graminis* to Antibiotics Produced by Fluorescent *Pseudomonas* spp. and Effect on Biological Control of Take–all of Wheat," *Applied and Environmental Microbiology* 61:2554–2559 (1995).

J.M. Raaijmakers, D.M. Weller and L.S. Thomashow, "Frequency of Antibiotic Producing Pseudomonas spp. in Natural Environments," *Applied and Environmental Microbiology* 63:881–887 (Mar. 1997).

L.S. Thomashow and D.M. Weller, "Current Concepts in the Use of Introduced Bacteria for Biological Disease Control: Mechanisms and Antifungal Metabolites," In: *Plant–Microbe Interactions*, vol. 1, (Eds) G. Stacey and N. Keen, Chapman and Hall, New York, N.Y., pp. 187–235 (1996).

P. Shanahan, D.J. O'Sullivan, P. Simpson, J.D. Glennon, and F. O'Gara, "Isolation of 2,4–Diacetylphloroglucinol from a Fluorescent Pseudomonad and Investigation of Physiological Parameters Influencing Its Production," *Applied and Environmental Microbiology* 58:353–358 (1992).

M.N. Vincent, L.A. Harrison, J.M. Brackin, P.A. Kovacevich, P. Mukerji, D.M. Weller and E.A. Pierson, "Genetic Analysis of the Antifungal Activity of a Soilborne *Pseudomonas aureofaciens* Strain," *Applied and Environmental Microbiology* 57:2928–2934 (1991).

B. Nowak–Thompson and S.J. Gould, "Production of 2,4–diacetylphlorolgucinol by the biocontrol agent *Pseudomonas fluorescens* Pf–5," *Can. J. Microbiol* 40:1064–1066 (1994).

C. Keel, U. Schnider, M. Maurhofer, C. Voisard, J. Laville, U. Burger, P. Wirthner, D. Haas and G. Defago, "Suppression of Root Disease by *Pseudomonas fluorescens* CHA0: Importance of the Bacterial Secondary Metabolite 2,4–Diacetylphloroglucinol," *Molecular Plant–Microbe Interactions* 5:4–13 (1992).

J.M. Raaijmakers, D.M. Weller and L.S. Thomashow, "Frequency of antibiotic–producing pseudonomads in take–all suppressive soils," American meeting of the American Pytopathological Society, Indianapolis, USA, *Phytopathology* (11 suppl) S36–S37 (1996).

J.G.K. Williams, A.R. Kubelik, K.J. Lival, J.A. Rafalski and S.V. Tingey, "DNA polymorphisms amplified primers are useful as genetic markers," *Nucleic Acids Research* 18:6531–6535 (1990).

*Primary Examiner*—Sandra E. Saucier
*Assistant Examiner*—Vera Afremova
(74) *Attorney, Agent, or Firm*—Margaret A. Connor; M. Howard Silverstein; John D. Fado

(57) ABSTRACT

Fluorescent *Pseudomonas* spp. are described which are effective for the control of diseases caused by the soil-borne fungus, *Gaeumannomyces graminis* (Gg), such as take-all, in small grain crops or turf grass. The subject biocontrol strains have a unique genotype as shown by a characteristic banding pattern, and exhibit root-colonizing ability which is characterized by both higher population density on roots and extended colonizing activity compared to known Gg-suppressive strains. A further property is the ability of a strain to duplicate the level of biocontrol obtained naturally in a take-all decline soil. Methods for isolation and identification of the strains and their use to control diseases caused by Gg are provided. In particular, strains of *P. fluorescens* NRRL B-21806 and NRRL B-21807.

13 Claims, 6 Drawing Sheets

SCREENING PROTOCOL

Step 1: Successive growth cycles of wheat to enrich for Phl producers

Step 2: Isolation of fluorescent Pseudomonads from roots of wheat cycled in TAD soil Step 3: Colony hybridization with specific probes to detect Phl producers Step 3a (optional): Confirmation of Phl producers by PCR Step 4: RAPD analysis to identify Phl producers with the definitive banding pattern

FIG.2

BIOCONTROL AGENTS FOR TAKE-ALL

This application is a continuation of application Ser. No. 08/974,938, filed Nov. 20, 1997, now abandoned which is incorporated herein by reference.

BACKGROUND OF THE INVENTION

1. Field of the Invention

The present invention relates to biocontrol of diseases caused by the soil-borne fungus *Gaeumannomyces graminis*. In particular, the invention relates to strains of fluorescent Pseudomonas species (spp.) which have unique root-colonizing ability for small grain crops and biocontrol activity for diseases caused by *Gaeumannomyces graminis* in small grain crops and take-all patch in turf grass. The invention further relates to isolation and identification of the unique strains, and application thereof to control plant diseases caused by *Gaeumannomyces graminis*.

2. Description of the Art

Widespread diseases of small grain crops and turf grass are caused by the soil-borne fungus *Gaeumannomyces graminis* (*Gg*), and result in significant economic losses due to reductions in crop yield. Take-all, a disease caused by *Gaeumannomyces graminis* var. *tritici* (*Ggt*) occurs in all wheat-growing regions of the world and is the most important root disease of wheat. Symptoms of wheat take-all include dark longitudinal lesions on roots; in severe cases, the entire root may become blackened with disease with the fungus migrating to the crown of the wheat plant (where the crown roots originate) and the tillers (stems). Severely infected wheat plants are identified in the field by their white heads which result when infection of the crown by the fungus cuts off water transport to upper plant parts causing the plant to die prematurely. Yield losses can be considerable up to 50% of the potential wheat yield. There are no resistant wheat cultivars and registered fungicides perform inconsistently. Further, growers are being increasingly challenged to grow wheat with minimum or no tillage to reduce soil erosion. These practices increase the severity of take-all and other root diseases. Although wheat is particularly susceptible to the take-all fungus, many other Gramineae such as barley, rye, and triticale can also be infected.

Traditionally, take-all has been controlled by a combination of crop rotation and tillage, practices which reduce the inoculum potential of the pathogen. However, because long rotations are often not economically feasible and tillage contributes to soil erosion, the trend in cereal production is toward less tillage and two or three wheat crops before a break. Both of these practices exacerbate take-all. There is no known source of genetic resistance in wheat against take-all, and methods of chemical control are limited. The need for agriculture to become more sustainable and less dependent on chemical pesticides has necessitated the development of alternative approaches to control take-all and other soil-borne diseases.

Other *Gg* fungi, for example, *Gaeumannomyces graminis* var. *avenae* (*Gga*) infects oats and grasses and have been identified as causing take-all patch in turf grasses such as bent grass. *Gaeumannomyces graminis* var. *graminis* (*Ggg*) infects some grasses and has been suggested as causing crown sheath rot in rice.

All agricultural soils show some degree of antagonism to *Ggt* and other soil-borne pathogens. This has been referred to as "general suppression" (N. Gerlagh, *Netherlands Journal of Plant Pathology* 74:(Suppl. 2) 1–97 (1968) or "general antagonism" (D. Hornby, *Annual Review of Phytopathology*, Annual Reviews Inc. Palo Alto, Calif. (1983), pp. 65–85). General antagonism results from the overall microbial activity in a soil. In addition, a "specific" suppression (biological control) of *Ggt* (known as take-all decline) develops in certain circumstances which is superimposed over "general suppression" and which results in a nearly complete control of take-all. Take-all decline (TAD) is a natural biological control of take-all, defined as the spontaneous reduction in disease and the increase in yield with extended monoculture of *Ggt*-susceptible small grain crops such as wheat and barley. TAD was first observed more than 50 years ago and is now recognized as a worldwide phenomenon. The similarity of TAD throughout the world is remarkable in view of the broad range of soil types, climates, and agronomic conditions under which wheat, barley, and other small grains are cultivated. Field studies have clearly indicated that the development of TAD follows a consistent pattern everywhere, requiring the continuous cultivation of a small grain and the presence of the take-all pathogen. Factors such as soil type and previous cropping history only seem to modulate the extent and speed of development of TAD. Despite the fact that take-all eventually declines, most growers abandon monculture prematurely because interim losses can be considerable. Once established, however, TAD permits a recovery in yield and persists as long as monoculture continues. Practical exploitation of TAD offers the potential as a natural biological control of take-all. However, to do this, the responsible mechanism(s) for TAD would need to be identified and applied. However, research to date has been mostly descriptive and no particular occurrence of TAD is yet fully understood. A similar decline of take-all patch caused by *Gga* occurs in established turf.

TAD has been extensively studied in an attempt to determine the mechanisms responsible for natural take-all suppression. The most common theories put forward to explain this phenomenon include changes in the microbiological status of the soil, build up of antagonistic bacteria, changes in the pathogenicity and population of the fungus, and presence of protective fungi (D. Hornby in "Take-All Decline: A Theorists's Paradise," *Soil-borne Plant Pathogens*, Ed. B. Schippers and W. Gams, Academic Press, New York (1979), pp. 133–156 and D. Hornby, *Annual Review of Phytopathology*, Annual Reviews Inc., Palo Alto, Calif. (1983), pp. 65–85). Hornby reviewed these explanations and concluded that no single mechanism could explain TAD worldwide, and this view has been universally accepted by those working in the field of disease suppressive soils.

The most widely held explanation for TAD is based on microbial interactions between the take-all pathogen and specific antagonistic root-associated microorganisms (R. J. Cook and A. D. Rovira, *Soil Biology and Biochemistry* 8: 269–273 (1976)). Several types of evidence support a role for microbial antagonism in the suppression of *Ggt*. For example, suppressiveness can be transferred by incorporation of a small amount (1–10% w/w) of a TAD (suppressive) soil into a take-all conducive soil. Furthermore, the suppressiveness of a TAD soil is eliminated by pasteurization of the soil with moist heat (60° C., 30 min.), by soil fumigation with methyl bromide or by growing crops which are non-hosts of the pathogen.

Studies of the microbial antagonism involved in TAD have focused on attempts to identify specific *Ggt*-antagonistic microorganisms and to transfer these organisms to soil to reproduce suppression. A wide variety of microorganisms have been tested given the prevailing idea that the specific strains responsible differ among TAD soils. Cook and Rovira, 1976, supra, originally hypothesized that among the antagonistic microorganisms the fluorescent Pseudomonas spp. have a key role in TAD. U.S. Pat. No. 4,456,684 describes Pseudomonas strains which suppress diseases caused by take-all and other *Gg* fungi and methods for selection and application of the strains.

Many of the most effective strains produced the antibiotic 2,4-diacetylphloroglucinol (Phl) (C. Keel et al., *Applied and Environmental Microbiology* 62:552–563 (1996)). Phl is a phenolic metabolite with activity against a variety of bacteria, viruses, and fungi, including the take-all pathogen (reviewed in L. S. Thomashow and D. M. Weller, In: G. Stacey and N. T. Keen (eds.) *Plant-microbe Interactions*, Vol. I, Chapman & Hall, Ltd. London, pp. 187–236 (1996)). J. M. Raaijmakers et al. (*Applied and Environmental Microbiology* 63:881–887 (1997)) report that Phl-producing fluorescent Pseudomonas spp. were present on roots of wheat grown in three TAD soils from Washington State (USA). In take-all conducive soils collected from sites near the TAD fields, Phl-producing fluorescent Pseudomonas. spp. were not detected or were detected at densities at least 40-fold lower than those in the TAD soils. Although use of microbial biocontrol agents holds great promise as a practical means to control soilborne pathogens, all published or patented biocontrol agents for take-all have the disadvantages of performing inconsistency, being soil-specific, and being unable to duplicate the level of control consistently observed in a TAD soil. No microorganism tested to date has demonstrated the disease control abilities expected of a strain involved in TAD. Thus, it is not surprising that no biocontrol agent for take-all has been commercialized. What is needed are effective biocontrol agents for take-all which duplicate the suppressiveness of a TAD soil and are effective independent of soil type, and perform consistently.

SUMMARY OF THE INVENTION

We have discovered unique biocontrol agents for control of the diseases caused by the soil-borne fungus *Gaeumannomyces graminis* (*Gg*) in small grain crops and turf grass. The invention encompasses unique strains of fluorescent Pseudomonas species (spp.) which suppress (inhibit the incidence of or reduce the incidence or severity of) diseases caused by *Gg*, such as take-all, at low doses, and have root-colonizing ability which is greater than any previous biocontrol agent of *Gg*. In addition, the root colonization ability and biocontrol activity of the strains are not affected by soil type.

The biocontrol agents of the invention provide biocontrol which is consistently greater than that of all known biocontrol agents for diseases caused by *Gg*, such as take-all. Additionally, the strains have the further unique property of being able to duplicate the level of biocontrol observed in a TAD soil.

The biocontrol agents of the invention comprise biologically pure cultures of strains of fluorescent Pseudomonas spp. which contain a biosynthetic locus which encodes for the production of the antibiotic 2,4-diacetylphloroglucinol, which have a unique genotype as shown by a characteristic unique Random Amplified Polymorphic DNA (RAPD) profile, exhibit biocontrol activity at dose levels 10 to 1000 times lower than take-all-suppressive microorganisms known heretofore, and exhibit superior root colonizing ability as demonstrated by 10 to 1000-fold higher population density and extended colonizing activity. We have found that exemplary strains of the invention have the ability to colonize roots at a population density averaging at least $10^5$ colony forming units per gram of root, including the rhizosphere soil, for at least 7 successive growth cycles. Such root-colonizing ability is unprecedented. Further, the novel strains are not affected by soil type.

The invention further comprises methods of isolation and identification of these unique strains. A protocol for screening of bacteria is shown in FIG. 2, and the screening method is described in detail, below.

A further aspect of the invention is application of the unique strains or compositions comprising the strains for biocontrol of plant diseases caused by *Gaeumannomyces graminis*. When used as a seed, soil, furrow treatment or drench, the unique strains of the invention have the ability to suppress *Gg* under field conditions. Application of the strains to seed or soil showed the unprecedented duplication of suppression of take-all equivalent to natural take-all decline (see Table 1, below), which has never been shown before. Further, because the strains suppress take-all at low dose levels, the strain can be grown and applied at a cost of nearly 10 to 1000-fold less than other currently existing biocontrol agent of take-all. In addition, because the strains are responsible for natural TAD, it is envisioned that they need only be applied only once in a field. All other biocontrol agents of take-all require repeated application.

In accordance with this discovery, it is an object of the invention to provide unique strains of fluorescent Pseudomonas spp. which provide biocontrol of the diseases caused by *Gg* which is greater than known biocontrol strains.

It is also an object of the invention to provide biocontrol strains that have root colonizing ability (higher root population density and extended activity) which is greater than any known biocontrol agent for take-all. This property is particularly valuable because it is known that for suppression of root diseases such as take-all, increases in root colonization result in greater and more consistent biocontrol activity.

Another object of the invention is the provision of biocontrol agents for control of diseases caused by *Gaeumannomyces graminis* in small grains and turf grass which are not affected by soil type.

It is a further object of the invention to provide methods based on RAPD analysis for selecting the strains of the invention having a characteristic banding pattern.

A still further object of the invention is the provision of methods for biologically controlling take-all in small grain crops and patch in turf grass using the strains of the invention and agricultural compositions which incorporate the strains.

Other objects and advantages of the invention will become readily apparent from the ensuing description.

BRIEF DESCRIPTION OF THE DRAWINGS

FIG. 2 shows a protocol for isolation and identification of the unique fluorescent Pseudomonas spp. of the invention from take-all suppressive soils.

DETAILED DESCRIPTION OF THE INVENTION

Biocontrol Agents of the Invention. The biocontrol agents of the invention comprise at least one biologically pure strain of fluorescent Pseudomonas spp. which has the following identifying characteristics: the strain contains a biosynthetic locus which encodes for the production of 2,4-diacetylphloroglucinol; it has a unique genotype as shown by a characteristic banding pattern described in detail, below, and in FIG. 1; it suppresses diseases caused by *Gg* in field-grown small grain crops or turf grass; and it exhibits root-colonizing ability which is characterized by both higher population density and extended colonizing activity compared to known *Gg*-suppressive strains.

Preferably, the strain has the following additional identifying characteristics: it's biocontrol activity (disease suppression ability) and root colonization ability are not affected by soil type and/or it suppresses *Gg* in small grain crops equivalent to a level of biocontrol obtained when the small grain crop is grown in a soil in a state of take-all decline, that is, it duplicates the level of biocontrol observed in a take-all decline soil.

Exemplary of the strains of the invention are *P. fluorescens* strains Q8r1-96, ML4.9-96, and L5.1-96.

Figure 1:
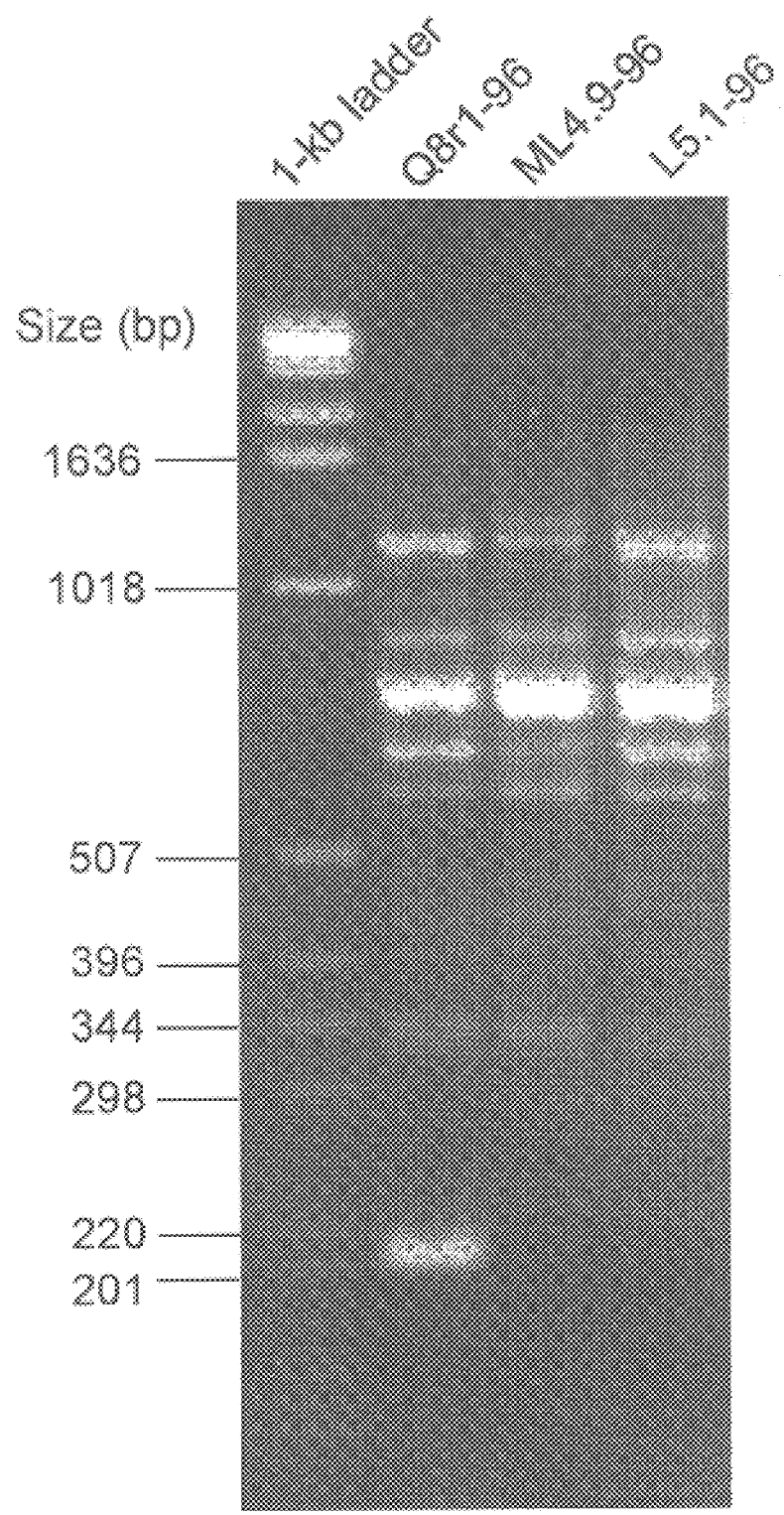
FIG. 1 is an image which shows the banding patterns (RAPD) of *P. fluorescens* strains Q8r1-96, ML4.9-96, and L5.1-96. Lane 1 shows a 1-kb ladder as a reference.

Characteristic Banding Pattern. The biologically pure fluorescent Pseudomonas spp. strains of the invention have an identifying characteristic banding pattern. This profile can be identified by RAPD-analysis with primer M13 as described in Example 1, below. FIG. 1 shows the banding patterns (RAPD) of *P. fluorescens* strains Q8r1-96, ML4.9-96, and L5.1-96, which are exemplary strains of the invention. Lane 1 shows a 1-kb ladder as a reference. As shown in FIG. 1, the bands shared by the strains are: 330±20 bp; 600 bp±50 bp; 700±50 bp; 800 bp±50 bp; 900 bp±50 bp, and 1100 bp±60 bp. The band at 800 bp±50 bp is the most intense.

For purposes of this invention, a strain has the characteristic banding profile of the invention if it has bands at 600 bp±50 bp; 700±50 bp; 800 bp±50 bp; 900 bp±50 bp using the conditions described in Example 1, below. In a preferred embodiment, the strain also has bands at 330±20 bp and 1100 bp±60 bp.

An alternative way to identify if a strain has the characteristic banding pattern of the invention is to carry out a side-by-side comparison in an agarose gel using *P. fluorescens* strain Q8r1-96 and the test strain and visually comparing the bands between about 600±50 and 900±50 base pairs. If the profile of the test strain matches the profile of strain Q8r1-96 in this region, then the test strain has the characteristic banding pattern encompassed by this invention.

Biocontrol activity. The biologically pure fluorescent Pseudomonas spp. strains of the invention have the ability to suppress (inhibit the incidence of or reduce the incidence or severity of) diseases caused by *Gg*, such as take-all, in small grain crops or turf grass. Tables 1, 2, and 4 in the Examples, below, present data showing biocontrol activity. As shown in Table 2 in Example 3, below, strain Q8r1-96 reduced the percentage of wheat plants infected with take-all in the field by 20%. As shown in Table 4 in Example 4, below, strain Q8r1-96 was shown to be nearly twice as effective at reducing take-all as *P. fluorescens* strain Q2-87 (a known suppressive Phl-producing strain) after 9 cycles of cropping wheat. As discussed below, Q8r1-96 duplicated the biocontrol of TAD soil.

Figure 3:
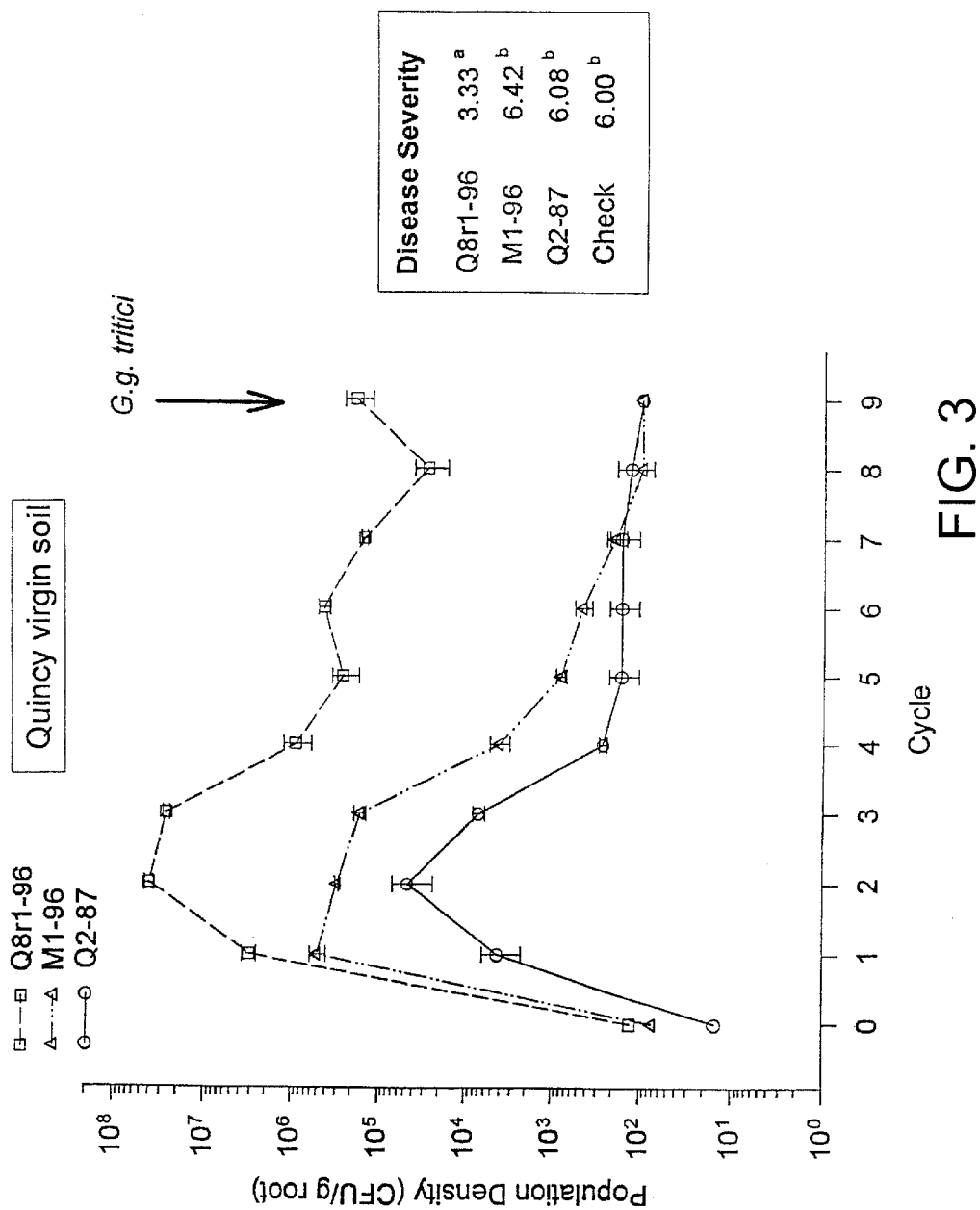
FIGS. 3–5 show the colonizing ability of the invention strain *P. fluorescens* Q8r1-96 compared to *P. fluorescens* strains M1-96 and Q2-87, (strains not in accordance with the invention) in Quincy virgin soil, Lind virgin soil, and Moses Lake virgin soil, respectively.

Colonizing ability. The biologically pure fluorescent Pseudomonas spp. strains of the invention show a unique colonizing ability which is characterized by both (a) higher population density on the roots and (b) extended colonizing activity compared to known suppressive strains. That is, the strains of the invention have the ability to both colonize and persist on the roots of small grains. As shown in the Examples, below, strains of the invention have the ability to colonize roots at a population density averaging at least about $10^5$ colony forming units (CFU)/gram of root, including the associated rhizosphere soil, for at least 7 successive growth cycles. FIG. 3 shows colonization of wheat (cv Penawawa) roots by Q8r1-96 during 9 cycles of wheat in Quincy virgin soil. By cycle 5, the population density of Q8r1-96 was nearly 1000-fold greater than that of *P. fluorescens* strains Q2-87 and M1-96 (strains not in accordance with the invention). Q8r1-96 also showed significantly greater population densities in the Land and Moses lake virgin soils in FIGS. 4 and 5.

For purposes of this invention, a strain has the characteristic colonizing ability of the invention if it colonizes roots of wheat at a population density averaging at least about $10^5$ CFU per gram of root including associated rhizosphere soil for at least 5 successive growth cycles under growth conditions described in Example 4, below.

Figure 6:
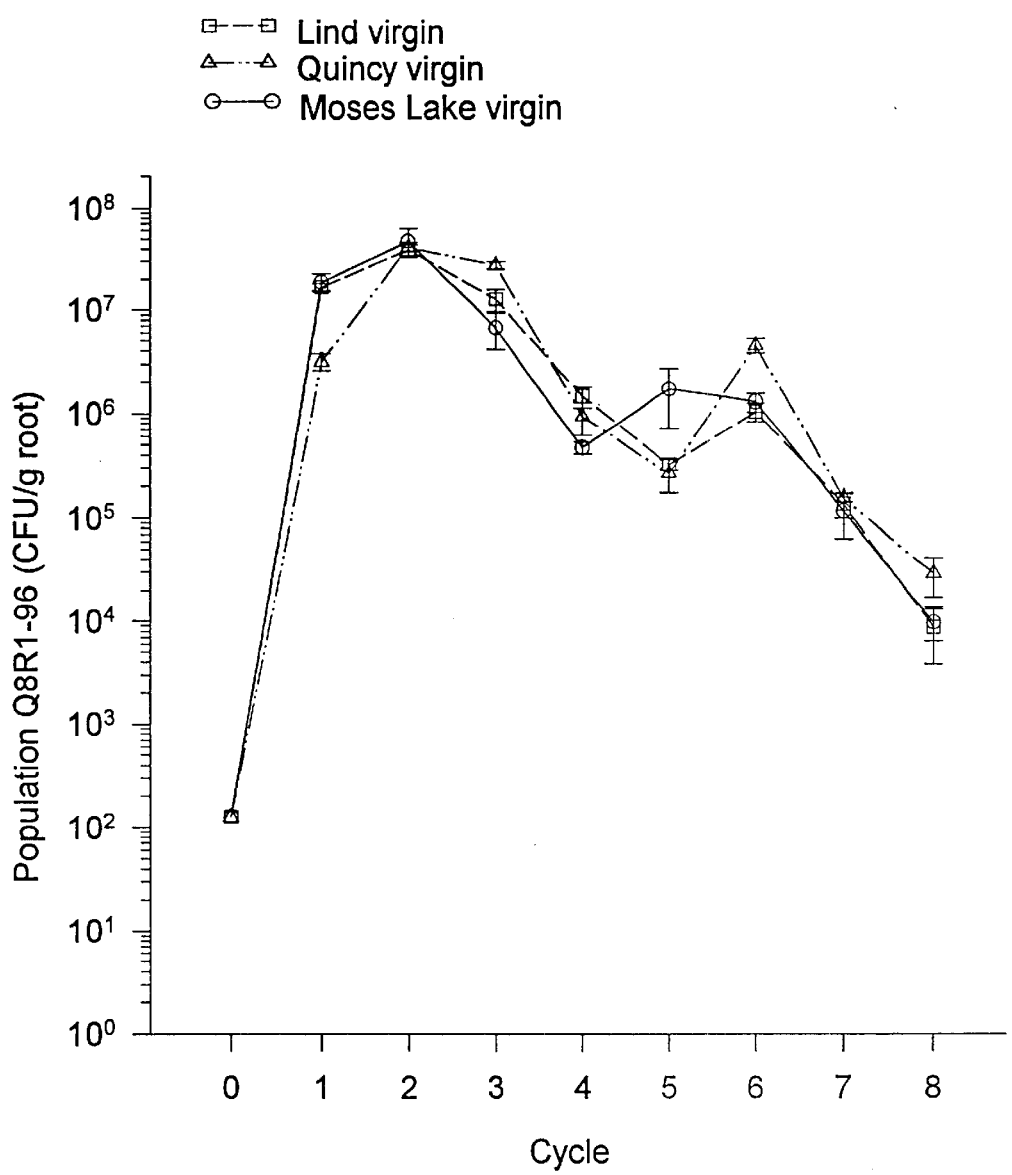
FIG. 6 shows the colonizing ability of the invention strain *P. fluorescens* Q8r1-96 in Quincy virgin soil, Lind virgin soil, and Moses Lake virgin soil.

Unaffected by Soil Type. In a preferred embodiment, a biocontrol strain of the invention has the further characteristic that its biocontrol activity and root colonization ability are not affected by soil type. As can be seen in FIG. 6, during 7 cycles, the populations densities of Q8r1-96 were not affected by soil type.

Duplication of Biocontrol of TAD Soil. A biocontrol strain of the invention is preferably further characterized by having the ability to suppress diseases caused by *Gg* in small grain crops that is equivalent to a level of biocontrol obtained when the small grain crop is grown in a soil in a state of take-all decline (TAD). That is, the strain has the ability to duplicate the level of biocontrol obtained in a take-all decline soil. As shown in Table 1 in Example 1, below, Q8r1-96 applied at a dose of $10^4$ colony forming units (CFU)/seed and then sown in Quincy virgin (conducive) soil was as effective at suppressing take-all as the Quincy TAD soil. In addition, Qr81-96 was as effective in Lind virgin (conducive) soil as Quincy TAD soil added at 10% w/w into the Lind virgin soil. This duplication of suppression of take-all equivalent to natural take-all decline is unprecedented.

Screening Method. The invention also encompasses methods for selecting the unique fluorescent Pseudomonas strains of the invention. Using our method, microorganism strains having the above-described characteristics are obtained, In brief, our method includes the steps of: (1) cultivating a small grain crop or turf grass in successive growth cycles in take-all suppressive soil (e.g., soil in a state of take-all decline) to enrich for fluorescent Pseudomonas spp. which contain a biosynthetic locus which encodes for the production of 2,4-diacetylphloroglucinol (also referred to as Phl-producing fluorescent Pseudomonas spp.); (2) isolating strains of potentially-suppressive fluorescent Pseudomonas bacteria; (3) screening the isolated strains to select strains which contain a biosynthetic locus which encodes for the production of 2,4-diacetylphloroglucinol by colony hybridization with a 2,4-diacetylphloroglucinolspecific DNA probe to detect Phl-producers; and (4) using RAPD analysis to select those strains having the characteristic banding pattern, described above. An optional step can be inserted after step 3 to confirm Phl production. FIG. 2 shows the screening protocol using wheat.

The following is a more detailed description of the selection method of the invention.

Step 1. Successive growth cycles to enrich for Phl producers.

In this step, a small grain crop or turf grass is cultivated in successive growth cycles in natural take-all suppressive soil to enrich for Phl-producing fluorescent Pseudomonas spp. as follows: (a) growing seeds of a small grain crop or growing turf grass in a soil in a state of take-all decline (TAD soil) in the greenhouse for at least 3 weeks and under conditions effective to support growth of said small grain crop or turf grass to obtain seedlings; (b) collecting the soil and roots of the small grain crop or turf grass seedlings grown in the soil and mixing them together; and (c) repeating steps (a) through (b) for at least a total of 4 successive cycles, wherein the mixture of step (b) is used to grow the seeds in the succeeding cycle.

Step 2. Isolation of fluorescent Pseudomonas spp. from roots cycled in TAD soils.

In this step, strains of potentially-suppressive fluorescent Pseudomonas bacteria are isolated from the roots and associated rhizosphere soil of the small grain crop or turf grass successively cultivated in step (1) by growing the strains on a Pseudomonas-selective medium for a time and under conditions effective for growth of Pseudomonads and selecting strains which grow on the medium.

Step 3. Colony hybridization with specific probes to detect Phl producers. In this step, strains isolated in step 2 are screened to select a strain which contains a biosynthetic locus which encodes for the production of 2,4-diacetylphloroglucinol (Phl) by hybridizing a colony of the strains with a 2,4-diacetylphloroglucinol-specific probe and selecting strains that hybridize to the probe. The selected individual colonies are picked, streaked, and restreaked until the strain is stable and pure, that is, it is a biologically pure culture. The strain can be stored in glycerol at −80° C. to keep it stable.

Step 3a (optional). Confirmation of Phl-producers by PCR.

In this optional step, confirmation of Phl producing strains is carried out using primers which amplify sequences within the Phl biosynthetic locus, and those strains that give a positive PCR reaction are selected.

Step 4. RAPD analysis to identify Phl-producers with the definitive banding pattern.

In this step, Random Amplified Polymorphic DNA analysis is carried out using primer M13 (Sequence: GGTGGTCAAG) (see Keel et al., supra). Primer M13 is available commercially from Operon Technologies Inc., Alameda, Calif. Strains which have bands at 600 bp±50 bp; 700±50 bp; 800 bp±50 bp; 900 bp±50 bp are selected. It is preferred that the strains also have bands at 330±20 bp and 1100 bp±60 bp.

Using our method we obtained biologically pure cultures of P. fluorescens strains Q8r1-96, L5.1-96, and ML4.9-96 which are exemplary of the strains of the invention.

Statement of Deposit. Biologically pure cultures of strains Q8r1-96, L5.1-96, and ML4.9-96 were deposited Jul. 8, 1997 under terms of the Budapest Treaty in the Agricultural Research Culture Collection (NRRL), 1815 North University Street, Peoria, Ill. 61604, and have been assigned the accession numbers NRRL B-21806, NRRL B-21807, and NRRL B-21808, respectively. Strains having the identifying characteristics of NRRL B-21806, NRRL B-21807, or NRRL B-21808 are encompassed by this invention. For the purpose of this invention, any isolate having the identifying characteristics of strains NRRL B-21806, NRRL B-21807, or NRRL B-21808, including subcultures and variants thereof which contain a biosynthetic locus which encodes for the production of the antibiotic 2,4-diacetylphloroglucinol and have the definitive banding pattern described above, and which retain the ability to suppress diseases caused by Gg in small grain crops or turf grass and retain the characteristic root-colonizing ability, are included. The term variants is defined herein to include transformants and mutants which having the aforenamed characteristics.

Growth of the Strains of the Invention. The fluorescent Pseudomonas spp. strains of the invention can be grown on any suitable solid or liquid bacteriological medium. An exemplary medium is King's medium B. Growth of the strains are effected under aerobic conditions at any temperature satisfactory for growth of the organism, i.e., from about 15° C. to 30° C.; the preferred temperature range is about 24° C. to 28° C. The pH of the nutrient medium is preferably about neutral, i.e., pH 6.7–7.2.

Maintenance of Stock Cultures. Each strain is maintained to keep it stable, such as by storing in glycerol at −80° C.

Application of Gg-Suppressive Strains. The microorganism strains of the invention are useful in controlling diseases of small grain crops or turf grass caused by Gg. Examples of small grain crops are wheat, barley, rye, and triticale. Examples of diseases caused by Gg are take-all disease caused by Ggt which is the most important root disease of wheat and which can also infect other Gramineae such as barley, rye, and triticale. Other Gg fungi include Gga which infects oats and grasses and which has been identified as causing take-all patch in turf grasses such as bent grass; and Ggg which infects some grasses.

To achieve biocontrol of diseases caused by Gg in small grain crops and turf grass, the crop or grass is grown in the presence of an effective suppressive amount of one or more fluorescent Pseudomonas strains of the invention. An effective biocontrol amount is defined as that quantity of biocontrol agent which suppresses (inhibits the incidence or reduces the incidence or severity of) diseases caused by Gg relative to that occurring in an untreated control. Optimally, the biologically pure culture is applied to obtain at least 15% less disease in the field grown small grain crop or turf grass compared to an untreated control. Biocontrol is carried out by applying an effective amount of the biocontrol agent to a plant, to a seed of a plant or to the locus of the plant or seed. For example, the strain can be applied as a seed, soil or furrow treatment or as a drench to turf or soil. Fresh cells or freeze-dried cells may be used.

The strain may be incorporated into compositions suitable for application to small grains or turf grass. It can be mixed with any agriculturally acceptable carrier or suitable agronomically acceptable carrier which does not interfere with the activity of the strain. Exemplary carriers are water, buffer, methylcellulose, ground peat or vermiculite. Where the strain is applied as a suspension or emulsion in a liquid carrier, the suspension or emulsion may optionally contain conventional additives such as surfactants or wetting agents as known in the art. The strain of the invention can also be formulated to include other biocontrol strains.

Exemplary application procedures and effective amounts are described below. The amount that will be within an effective range in a particular instance can be determined by experimental tests.

For seed treatment of small grain or turf, bacteria are added to a suspension containing 0.5–2.0% methylcellulose to minimize desiccation of the bacteria and promote adherence to the seed. The suspension is added to the seeds and mixed so that each seed is coated with about $10^2$ to $10^6$ CFU per seed. In general, the preferred amount is about $10^4$ to $10^6$ CFU per seed. Treated seeds are air dried.

For soil treatment, bacteria are suspended in water or buffer and applied during the first watering of the soil to give about $10^2$ to $10^6$ CFU per gram of soil. For turf, 2 ml of a drench containing about $10^2$ to $10^6$ bacteria per ml is added to about a 1-cm diameter plug of grass.

Where the carrier is a solid, e.g., peat or vermiculite, a typical formulation is about $10^7$ to $10^9$ CFU per gram of carrier. Where the carrier is a liquid, a typical formulation is about $10^8$ to $10^{10}$ CFU per ml of carrier. For a freeze-dried formulation, a typical amount is about $10^{10}$ to $10^{11}$ CFU per gram formulation. Freeze dried formulations may contain additives as known in the art.

EXAMPLES

The following examples are intended only to further illustrate the invention and are not intended to limit the scope of the invention which is defined by the claims.

Example 1

The following example describes the selection of fluorescent Pseudomonas spp. of the invention.

Overview. *Pseudomonas fluorescens* strains Q8r1-96, L5.1-96, and ML4.9-96 were isolated in 1996 from roots of wheat grown in soils collected from agricultural fields near, respectively, Quincy, Lind, and Moses Lake, Wash. (USA) that are in the state of take-all decline (TAD). Q8r1-96 was isolated from roots of wheat grown in Quincy TAD soil for 8 successive cycles of 3 weeks each; L5.1-96 from roots of wheat grown in Lind TAD soil for 5 successive cycles of 3 weeks each; ML4.9-96 from roots of wheat grown in Moses Lake TAD soil for 4 successive cycles of 3 weeks each. The protocol for isolation of these strains is described in FIG. 2.

The following is a detailed description of the soils and the isolation and characterization techniques.

Soils. The three different soils were obtained from agricultural fields in the state of TAD near Quincy, Lind, and Moses Lake, Wash. (USA). All three soils are suppressive to take-all of wheat. In 1995, the Lind TAD field had been cropped continuously to wheat for 28 years. In 1980, the TAD fields at Quincy and Moses Lake had been cropped continuously to wheat for 22 years; between 1980 and 1995 other crops besides wheat also were grown. The soils were collected in March 1995 from the upper 30 cm of the soil profile, air-dried for 1 week and passed through a 0.5-cm mesh screen prior to use. Their physical and chemical properties were determined by the Analytical Sciences Laboratory, University of Id.

Step 1: Successive growth cycles of wheat to enrich for Phl producers.

Twelve wheat seeds were sown in square PVC pots (8 cm high, 7.5 cm wide) containing 200 g of sieved natural soil (Quincy, Lind, or Moses Lake TAD soil) and 50 ml of water supplemented with metalaxyl (Novartis, Greensboro, N.C.) at 2.5 mg ml$^{-1}$ active ingredient to control Pythium root rot. Pseudomonads are not affected by this fungicide. A 1-cm layer of soil was spread on top of the seeds. Plants were grown in a controlled-environment chamber at 16° C. with a 12-hour photoperiod. Pots received 50 ml of dilute (2:3, vol/vol) Hoaglund's solution (macro-elements only) twice a week. After 3 to 4 weeks of growth, the shoots of the plants were excised at the soil surface, and the soil and associated root system was decanted into a plastic bag and shaken vigorously to aerate and mix. This 'cultivated' soil was stored for 1 week at 15° C., returned to the same pot, and then replanted with twelve wheat seeds. This process of plant growth and harvesting was repeated for at least four and up to eight successive cycles, at which time four randomly selected plants were harvested from each replicate and root samples were prepared to determine the population size of antibiotic-producing fluorescent Pseudomonas spp. For each soil, four replicates were used.

Step 2: Isolation of fluorescent Pseudomonas spp. from roots of wheat cycled in TAD soils.

Four randomly selected plants grown in step 1 were harvested from each replicate, and loosely adhering soil was removed from the roots by gently shaking. 1.0 g of roots and associated rhizosphere soil was suspended in 5.0 ml of sterile water and shaken vigorously for 1 minute on a Vortex mixer. The samples were subsequently sonicated in a ultrasonic cleaner for 1 minute, and then serial dilutions of the root wash were plated onto King's medium B [KMB] agar (Proteose peptone, 20 g; glycerol, 10 ml; $K_2HPO_4$, 1.5 g; $MgSO_4$, 1.5 g; agar, 15 g; $H_2O$, 1000 ml) supplemented with cycloheximide (100 μg ml$^{-1}$), chloramphenicol (13 μg ml$^{-1}$) and ampicillin (40 μg ml$^{-1}$) [KMB$^+$]. Plates were incubated at 25° C., and colonies were enumerated after 48 hours. Colonies of fluorescent Pseudomonas spp. were differentiated from non-fluorescent colonies under UV light (wavelength 366 nm).

Step 3: Colony hybridization with specific probes to detect Phl producers.

The number of fluorescent Pseudomonas spp. that harbor the genes for Phl was determined by colony hybridization. Transfer of bacterial colonies to Hybond-N$^+$ nylon membranes (Amersham) was performed by standard methods. After air drying, the membranes were baked for 1 hour at 80° C. in a vacuum oven. To remove bacterial cell debris, membranes were washed for 1.5 hours at 42° C. in a solution containing 2×SSPE (20 mM $NaH_2PO_4$ [pH 7.4], 0.36 M NaCl, 2 mM EDTA), 0.1% sodium dodecyl sulfate (SDS) and pronase (100 μg ml$^{-1}$) and washed again for 1 hour at 56° C. in 2×SSPE and 0.1% SDS. Hybridizations were performed by standard methods. High stringency conditions consisted of prehybridization for 1.5 hour at 65° C., hybridization for 12 hours at 65° C., membrane washing twice each for 5 minutes with 2×SSC and 0.1% SDS at room temperature, and membrane washing twice each for 30 minutes with 0.1×SSC and 0.1% SDS at 65° C.

Probes were generated from sequences within, the biosynthetic locus for 2,4-diacetylphloroglucinol (GenBank accession no. U41818). The probe was developed from sequences within Phl D of Q2-87 by random primed labeling of PCR fragments using the nonradioactive DIG system (Boehringer Mannheim). The hybridized probes were immunodetected with anti-digoxigenin-AP-Fab fragments and were visualized with the colorometric substrates nitroblue tetrazolium salt and 5-bromo-4-chloro-3-indolylphosphate, according to protocols provided by the supplier.

In order to isolate Phl producers, the signals on the membrane were aligned with the colonies on the agar plate. Each individual colony which gave a signal on the membrane was picked, streaked, and restreaked until the strain was stable and pure, that is, it is a biologically pure culture. Each strain was stored in glycerol at −80° C. to keep it stable.

Step 3a (optional): Confirmation of Phl-producers by PCR. This optional step allows false positives from the colony hybridization to be eliminated from analysis.

Heat-lysed bacterial suspensions used in PCR analysis were prepared from cultures grown on KMB for 48 hours at 25° C. Two bacterial colonies (2 mm diam) were suspended in 100 μl lysis solution (0.05 M NaOH, 0.25% SDS) and incubated for 15 min at 100° C. The suspension was centrifuged for 1 min at 12,000 rpm and diluted 50-fold in sterile distilled water. Five μl of the diluted suspension were used in each reaction.

Primers and PCR analysis. The oligonucleotide primers used in the PCR were developed from sequences within the biosynthetic locus for 2,4-diacetylphloroglucinol (Phl) of *P. fluorescens* Q2-87 (GenBank accession no. U41818). Primers were synthesized by Operon Techn. Inc. (Alameda, Calif.). Primers Phl2a (Sequence: GAGGACGTCGAAGACCACCA) and Phl2b (Sequence: ACCGCAGCATCGTGTATGAG) were developed from sequences within phlD, which predicts a protein of 349 amino acids that is homologous to chalcone synthase from plants.

PCR amplification was carried out in a 25-μl reaction mixture, which contained 5 μl of a diluted heat-lysed cell suspension, 1×GeneAmp PCR buffer (Perlin Elmer Corp., Norwalk, Conn.), 200 μM each of dATP, dTTP, dGTP, and dCTP (Perkin Elmer), 20 pmole of each primer, and 2.0 U of AmpliTaq DNA polymerase (Perkin Elmer). Each mixture was covered with one drop of mineral oil. Amplifications were performed in a Perkin Elmer Thermal Cycler 480. The PCR program consisted of an initial denaturation at 94° C. for 2 min followed by 30 cycles of 94° C. for 60 s, 67° C. for 45 s, and 72° C. for 60 s. Samples (9 μl) of the PCR products were separated on a 1.2% agarose gel in 1×TBE buffer (90 mM Tris-borate, 2 mM EDTA (pH 8.3)) at 75 V for 3 hours. The gel was stained with ethidium bromide for 30 minutes, and the PCR products were visualized using a UV transilluminator.

Step 4: RAPD analysis to identify Phl-producers with the definitive banding pattern. RAPD-analysis Random Amplified Polymorphic DNA) with primer M13 was performed for clustering the different Phl-producing fluorescent Pseudomonas strains isolated from roots of wheat grown in Quincy, Lind and Moses Lake TAD soil.

Amplification of the DNA was carried out in a 25-μl reaction mixture, which contained 5 μl of a diluted heat-lysed cell suspension, 1×GeneAmp PCR buffer (Perkin Elmer Corp., Norwalk, Conn.), 200 μM each of dATP, dTTP, dGTP, and dCTP (Perkin Elmer), 80 pmole of primer M13, and 2.0 U of AmpliTaq DNA polymerase (Perkin Elmer). Each mixture was covered with one drop of mineral oil. Amplifications were performed in a Perkin Elmer Thermal Cycler 480. The PCR program consisted of an initial denaturation at 94° C. for 1 min 30 sec followed by 2 cycles of 94° C. for 30 sec, 36° C. for 30 sec, 72° C. for 2 min, followed by 40 cycles of 94° C. for 20 sec, 36° C. for 15 sec, 45° C. for 15 sec, 72° C. for 1 min 30 sec, followed by 1 cycle of 72° C. for 10 min. Samples (9 μl) of the PCR products were separated on a 2.5% agarose gel in 1×TBE buffer (90 mM Tris-borate, 2 mM EDTA (pH 8.3)) at 75 V for 5 hours. The gel was stained with ethidium bromide for 60 minutes, and the PCR products were visualized using a UV transilluminator.

The biologically pure fluorescent Pseudomonas strains of the invention show a unique banding pattern as demonstrated by RAPD-analysis with primer M13. FIG. 1 shows the banding patterns (RAPD) of *P. fluorescens* strains Q8r1-96, ML4.9-96, and 15.1-96. Lane 1 shows a 1-kb ladder as a reference. As shown in FIG. 1, the bands shared by the strains of the invention are: 330±20 bp; 600 bp±50 bp; 700±50 bp; 800 bp±50 bp; 900 bp±50 bp, and 1100 bp±60 bp.

Example 2

The following example illustrates duplication of TAD using a biocontrol strain of the invention.

*P. fluorescens* strain 8r1-96 was isolated and propagated as described above in Example 1. The bacteria were suspended in 0.5% methylcellulose and mixed with wheat seed (cv. Penawawa) to give a dose of $10^4$ CFU per seed. Seed used as controls received only methylcellulose. Quincy Virgin, Quincy TAD, Pullman conducive and Pullman TAD soils were amended with 0.5% (w/w) of oat grain inoculum (sized 0.25–0.5 mm) of the take-all pathogen. Four treated seed were sown in square plastic pots (3 cm×3 cm) containing 50 g of sieved natural soil and wetted with water supplemented with metalaxyl (Novartis, Greensboro, N.C.) at 2.5 mg/ml active ingredient to control Pythium. Plants were grown in a controlled-environmental chamber at 16° C. with a 12-hour photoperiod. Pots received dilute (2:3 v/v) Hoaglund's solution (macro-elements) twice a week. After four weeks of growth plants were harvested, root disease was assessed and shoots were weighed and measured.

The results are tabulated below and show that strain Q8r1-96 introduced into Quincy Virgin or Pullman conducive soil provides the same amount of disease suppression as Quincy TAD and Pullman TAD soils, and Quincy TAD transferred into Pullman conducive. Strain Q8r1-96 did not increase the suppressiveness of Pullman TAD soil.

TABLE 1

Effect of Phl-producing *Pseudomonas fluorescens* Q8r1 −96 and of transferred Quincy TAD soil on the severity of take-all in natural soils

| Treatments[u] | Phl producers[v] (cfu g$^{-1}$ root) | Disease[v,w] severity | Plant weight[v] (mg) | Shoot height[v] (mm) |
|---|---|---|---|---|
| Experiment 1 | | | | |
| Quincy virgin | not detected[x] | 4.2 a | 180 a | 106 a |
| Quincy virgin + Q8r1 −96 | 4.6 × $10^6$ a | 3.1 b | 262 b | 133 b |
| Quincy TAD | 3.7 × $10^5$ b | 2.5 b | 281 b | 139 b |

TABLE 1-continued

Effect of Ph1-producing *Pseudomonas fluorescens* Q8r1 –96 and of transferred Quincy TAD soil on the severity of take-all in natural soils

| Treatments[u] | Ph1 producers[v] (cfu g$^{-1}$ root) | Disease[v,w] severity | Plant weight[v] (mg) | Shoot height[v] (mm) |
|---|---|---|---|---|
| Experiment 2 | | | | |
| Pullman Cond | not detected | 3.8 a | 212 a | 142 a |
| Pullman Cond + Quincy TAD (9:1)[y] | 4.5 × 10$^5$ a | 2.1 b | 335 b | 181 b |
| Pullman Cond + Q8r1 –96 | 4.5 × 10$^7$ c | 2.5 b | 288 b | 172 b |
| Pullman TAD | 1.3 × 10$^6$ b | 1.9 b | 336 b | 184 b |
| Pullman TAD + Quincy TAD (9:1)[y] | 3.5 × 10$^5$ a | 2.3 b | 286 b | 177 b |
| Pullman TAD + Q8r1 –96 | 3.4 × 10$^7$ c | 2.3 b | 306 b | 178 b |

[u]The Quincy virgin and Pullman Cond soils are both conducive to take-all of wheat, whereas the complementary TAD soils are suppressive to take-all. Quincy virgin and Quincy TAD soils had previously been cultivated to wheat for six successive cycles of four weeks each to activate the microflora. The Pullman Cond and the Pullman TAD soil were obtained directly from fields grown to wheat. All soils were amended with 0.5% (wt/wt) of an oat grain inoculum of the take-all pathogen. Wheat seeds treated with Q8r1 –96 received a dose of 10$^4$ cfu seed$^{-1}$.
[v]Population sizes of introduced strain Q8r1 –96 or of naturally occurring Ph1-producing fluorescent Pseudomonas spp., disease severity, plant fresh weight, and shoot height were determined after four weeks of plant growth. Mean values of six replicates of two plants each are presented. Differences between treatments in population densities of PHl-producing Pseudomonas spp., plant fresh weight, and shoot height were determined by analysis of variance followed by Tukey's Studentized Range Test. Differences in disease severity were analyzed by Wilcoxon Rank Sum test. For each experiment and for each parameter, mean values with different letters indicates a statistically significant difference ($\alpha$ = 0.05)
[w]Severity of take-all was rated on a 0–8 scale (0 = no disease, and 8 = dead plant).
[x]Below lower limit of detection of 10$^4$ cfu g$^{-1}$ root
[y]The Pullman Cond and Pullman TAD soils were each mixed with Quincy TAD soil in a 9:1 ratio (wt/wt)

Example 3

The following example describes biocontrol of take-all in field grown wheat. Pseudomonas fluorescens Q8r1-96 was tested in a commercial field at Almoto, Wash. The field used had been cropped to wheat the previous year and was naturally infested with take-all.

Experimental. Spring wheat (cv. Alpowa) was sown no-till on winter wheat stubble. *P. fluorescens* strain Q8r1-96, isolated and propagated as described above in Example 1, in a suspension of 1.5% methylcellulose was applied to Alpowa spring wheat seeds at a dose between about 1×10$^5$ and 1×10$^6$ CFU per seed. The controls consisted of wheat seed left untreated. In one control, denoted as "fumigated" in Table 2, the nontreated seed was sown into soil which had been fumigated with methyl bromide to eliminate the pathogen and to create a "healthy" control. In the other control, denoted as "control," nontreated seed was sown into the natural soil to create a diseased control. Treatment plots were 8 rows (spaced 1 foot apart) by 25 feet long. The wheat was harvested 135 days after planting.

Results. The results are shown in Table 2, below. As can be seen from the data, strain 8r1-96 decreased the number of infected plants by 20%.

TABLE 2

| Treatments | Plants Infected with Take-all (%)[a] |
|---|---|
| Control | 69.3A |
| Q8r1-96 | 48.0B |
| Fumigated | 13.3C |

[a]Means followed by the same letter are not significantly different at P = 0.1. LSD = 21.1

Example 4

The following example demonstrates the superior colonizing ability of the strains of the invention.

The invention strain *Pseudomonas fluorescens* Q8r1-96 was compared to *P. fluorescens* strains M1-96 and Q2-87 (not in accordance with the invention). All three strains produce the antibiotic 2,4-diacetylphloroglucinol, and show physiological traits and substrate utilization patterns typical of *P. fluorescens* as described in Bergey's Manual (see Table 3, below). However, the strains of the invention exemplified by Q8r1-96 have a characteristic RAPD banding pattern that is not shared by the non-invention strains.

TABLE 3

| | Q8r1-96 | Q2-87 |
|---|---|---|
| Gram stain | – | – |
| Shape | Rod | Rod |
| Fluorescent pigment | + | + |
| Oxidase | + | + |
| Arginine dihydrolase | + | + |
| Glucose fermentation | – | – |
| β-galactosidase | – | – |
| Gelatin hydrolysis | – | + |
| Denitrification | + | + |
| Utilization of: | | |
| D-glucose | + | + |
| L-arabinose | + | + |
| Sucrose | + | + |
| Propionate | + | + |
| Butyrate | – | – |
| Sorbitol | + | + |
| Adonitol | – | – |
| D-mannitol | + | + |
| N-acetyl-D-glucosamine | + | + |
| Maltose | – | – |
| D-gluconate | + | + |
| Caprate | + | + |
| Adipate | – | – |
| L-malate | + | + |
| Citrate | + | + |
| Phenylacetate | – | – |

In these studies assessing colonizing ability, each strain was applied individually into Quincy virgin soil, Lind virgin soil, and Moses Lake virgin soil at a dose of 100 CFU (bacterial cells) per gram of soil (pot size used was 8 cm high and 7.5 cm wide). Wheat (cv. Penawawa) was grown in each soil for 3 weeks, and the plants were harvested and bacterial populations on the roots determined by dilution plating.

The soil and associated root system was decanted into a plastic bag and shaken to aerate and mix the soil. One week after harvest each soil was returned to the same pot and again sown to wheat. Thus, each cycle between planting lasted 4 weeks.

Results. FIG. 3 shows the population density (CFU/g root) of the three strains in Quincy virgin soil after 9 cycles. As can be seen from the data, even after 9 cycles, strain Q8r1-96 shows population densities greater than $10^5$ CFU/g root. In contrast, strains M1-96 and Q2-87 (not in accordance with the invention) have dropped to $10^2$ CFU/g root. As can be seen from the data, the colonizing ability of the invention strain is superior compared to the other biocontrol strains; the invention strain colonizes the roots at a significantly higher level and has extended colonizing activity.

Comparison of biocontrol activity in Quincy Virgin soil. At the ninth cycle, inoculum of Ggt was added to the soil in the form of colonized oat grains. The inoculum was pulverized and sieved and particles 0.25 to 0.50 mm in size were mixed into the soil at a concentration of 0.5% (w/w). Take-all disease was rated on a scale of 0–8 as described below. Bacteria were compared to a control (check) in which no bacteria had been added to the soil. The plants were grown in pots (8 cm high and 7.5 cm wide) for 4 weeks. The data is shown in the Table 4, below. As can be seen from the Table, only Q8r1-96 (the invention strain) suppressed disease. The plants treated with non-invention strains showed the same amount of disease as the control (untreated plants). The superior suppression of invention strain Q8r1-96 (in the ninth cycle) can be attributed to the superior root colonizing ability and persistence of the invention strain, and shows how aggressive the strain is as a biocontrol agent.

TABLE 4

| Strain | Disease Severity[1] |
|---|---|
| Q8r1-96 | 3.33a[2] |
| M1-95[3] | 6.42b |
| Q2-87[3] | 6.08b |
| Check | 6.00b |

[1]Take-all was evaluated on a scale of 0 to 8 (Ownley et al., Phytopathology 82:178–184 (1992)), where: 0 no disease evident; 1 < 10% root area with black lesions; 2 10–25% root area with black lesions; 3 > 25% root area with black lesions and one root with lesions at base of stem; 4 = more than one root with lesions at base of stem; 5 ail roots with lesions at base of stem, at least one lesion on lower stem, but no leaf chlorosis; 6 many lesions on stem and the first true leaf chlorotic; 7 all leaves chlorotic and plant severely stunted; 8 plant dead or nearly so.
[2]Means followed by the same letter are not significantly different, P = 0.05.
[3]Not in accordance with the invention, for comparison purposes only.

Figure 4:
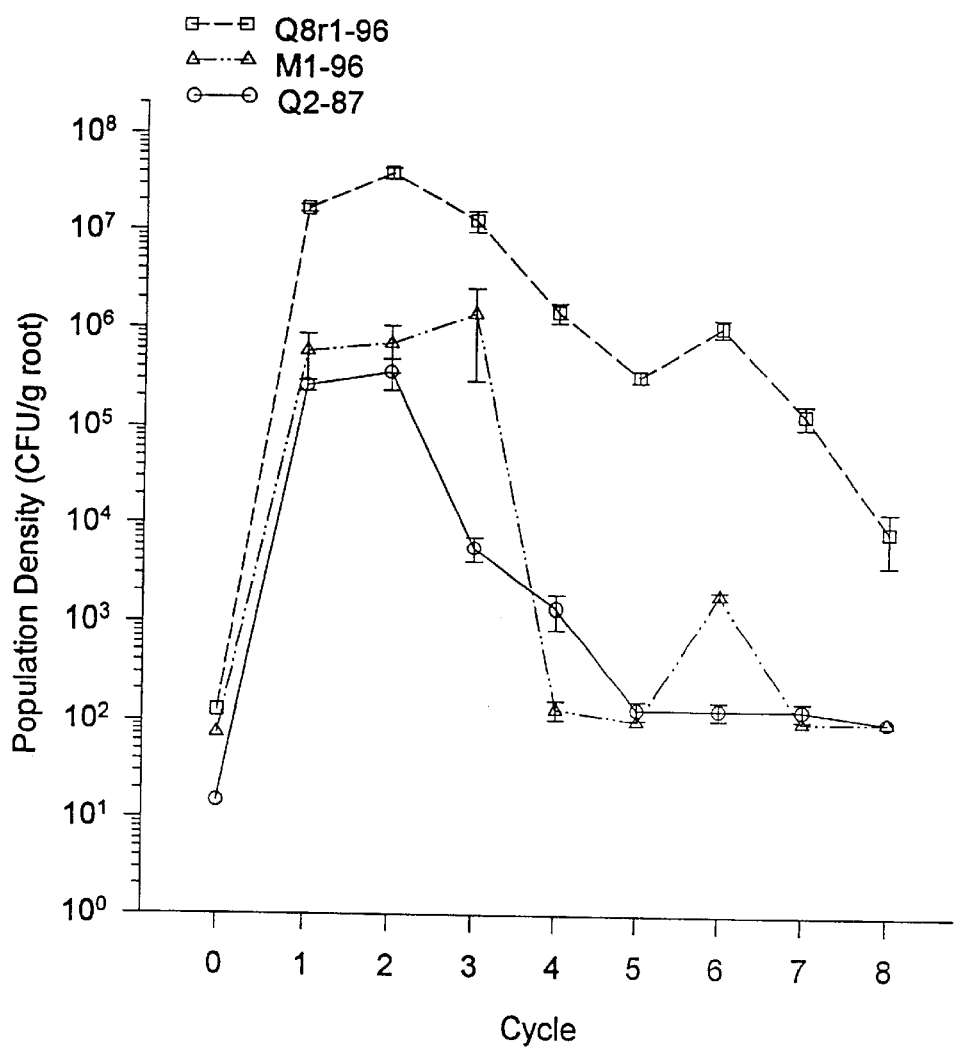
Figure 5:
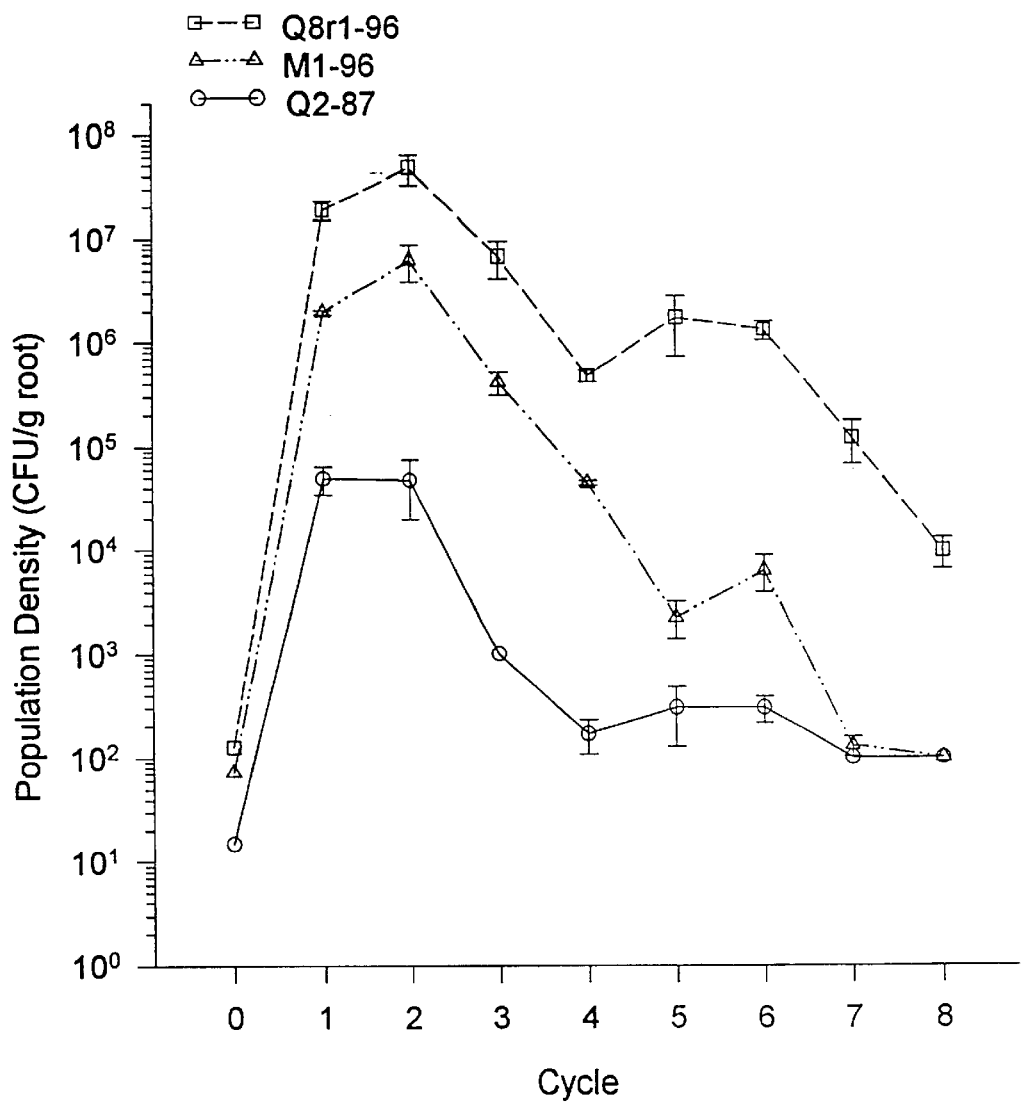

FIGS. 4–5 show the population density (CFU/g root) of the three strains in Lind and Moses Lake virgin soil, respectively, after 7 cycles. As can be seen from the data, even after 7 cycles, the population density of strain Q8r1-96 is greater than $10^5$ CFU/g root. In contrast, strains M1-96 and Q2-87 (not in accordance with the invention) have dropped to $10^2$ CFU/g root. As can be seen from the data, the colonizing ability of the invention strain is superior to the other strains; it colonizes the roots at a significantly higher level and has extended colonizing activity. The greater colonization results in greater biocontrol compared to the non-invention strains.

FIG. 6 shows the colonizing ability of the invention strain P. fluorescens Q8r1-96 in Quincy virgin soil, Lind virgin soil, and Moses Lake virgin soil. As can be seen from the data, the invention strain is not affected by soil type.

It is understood that the foregoing detailed description is given merely by way of illustration and that modification and variations may be made within, without departing from the spirit and scope of the invention.

What is claimed is:

1. A biologically pure culture of a fluorescent Pseudomonas strain which has all the identifying characteristics of *P. fluorescens* NRRL B-21806 or NRRL B-21807.

2. The biologically pure culture of claim 1 which further includes an agricultural carrier.

3. A method of controlling disease in a small grain crop or turf grass caused by *Gaeumannomyces graminis* fungus, which comprises growing said small grain crop or turf grass in the presence of an effective biocontrol amount of a biologically pure culture of a fluorescent Pseudomonas strain of claim 1.

4. The method of claim 3 wherein seed of said small grain crop is treated with an effective *Gaeumannomyces graminis*-biocontrol amount of said strain prior to said growing.

5. The method of claim 3, wherein soil or furrow for growing said small grain crop or turf grass is treated with an effective *Gaeumannomyces graminis*-biocontrol amount of said strain prior to said growing.

6. The method of claim 3 wherein said turf grass is treated with a bacterial treatment solution which comprises an effective *Gaeumannomyces graminis*-biocontrol amount of said strain and a suitable liquid carrier.

7. The method of claim 4 wherein said seed has a concentration of said strain of about $10^2$ to $10^6$ CFU per seed.

8. The method of claim 6 wherein said treatment solution has a concentration of said strain of about $10^8$ to $10^{10}$ CFU per ml of solution.

9. An agricultural composition for controlling disease in small grain crops or turf grass caused by *Gaeumannomyces graminis*, said composition comprising a suitable carrier and an *Gaeumannomyces graminis*-effective biocontrol amount of a biologically pure culture of a fluorescent Pseudomonas which has all the identifying characteristics of NRRL B-21806 or NRRL B-21807.

10. The agricultural composition of claim 9, wherein said carrier is selected from the group of water, buffer, methylcellulose, peat, and vermiculite.

11. The agricultural composition of claim 9 wherein said culture is in a concentration of about $10^8$ to $10^{10}$ CFU per ml of liquid carrier or $10^7$ to $10^9$ per gram of solid carrier.

12. A seed of a small grain crop having applied thereto an effective *Gaeumannomyces graminis*-biocontrol amount of a biologically pure culture of claim 1.

13. The seed of claim 12 where said seed has a concentration of said culture of about $10^2$ to $10^5$ CFU per seed.

* * * * *

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
      (A) LENGTH: 10 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "M13 primer"

(iii) HYPOTHETICAL: NO (iv) ANTI-SENSE: NO (ix) FEATURE:
      (A) NAME/KEY: misc_feature
      (B) LOCATION: 1..10

(x) PUBLICATION INFORMATION:
      (A) AUTHORS: Keel, C

-continued

```
            Weller, D M
            Natsch, A
            DeFago, G
            Cook, R J
            Thomashow, L S
    (B) TITLE: Conservation of the
        2,4-Diacetylphloroglucinol Biosynthesis Locus
        among Fluorescent Pseudomonas Strains from Diverse
        Geographic Locations
    (C) JOURNAL: Appl. Environ. Microbiol.
    (D) VOLUME: 62
    (E) ISSUE: 2
    (F) PAGES: 552-563
    (G) DATE: 1996
    (K) RELEVANT RESIDUES IN SEQ ID NO:1: FROM 1 TO 10

(xi) SEQUENCE DESCRIPTION: SEQ ID NO:1:

GGTGGTCAAG                                                           10

(2) INFORMATION FOR SEQ ID NO:2:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Phl2a"

(iii) HYPOTHETICAL: NO (iv) ANTI-SENSE: NO (x) PUBLICATION INFORMATION:
        (A) AUTHORS: Raaijmakers, Jos M
            Weller, David M
            Thomashow, Linda S
        (B) TITLE: Frequency of Antibiotic-Producing Pseudomonas
            spp. in Natural Environments
        (C) JOURNAL: Appl. Environ. Microbiol.
        (D) VOLUME: 63
        (E) ISSUE: 3
        (F) PAGES: 881-887
        (G) DATE: March-1997
        (K) RELEVANT RESIDUES IN SEQ ID NO:2: FROM 1 TO 20

(xi) SEQUENCE DESCRIPTION: SEQ ID NO:2:

GAGGACGTCG AAGACCACCA                                                20

(2) INFORMATION FOR SEQ ID NO:3:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Phl2b"

(iii) HYPOTHETICAL: NO (iv) ANTI-SENSE: NO (x) PUBLICATION INFORMATION:
        (A) AUTHORS: Raaijmakers, Jos M
            Weller, David M
            Thomashow, Linda S
        (B) TITLE: Frequency of Antibiotic-Producing Pseudomonas
            spp. in Natural Environments
        (C) JOURNAL: Appl. Environ. Microbiol.
        (D) VOLUME: 63
        (E) ISSUE: 3
        (F) PAGES: 881-887
```

(G) DATE: March-1997

(xi) SEQUENCE DESCRIPTION: SEQ ID NO:3:

ACCGCAGCAT CGTGTATGAG                                                    20

(2) INFORMATION FOR SEQ ID NO:4:

(i) SEQUENCE CHARACTERISTICS:
        (A) LENGTH: 7198 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Pseudomonas fluorescens (ix) FEATURE:
        (A) NAME/KEY: CDS
        (B) LOCATION: complement (1810..2859)
        (D) OTHER INFORMATION: /product= "PhlD"

(x) PUBLICATION INFORMATION:
        (A) AUTHORS: Thomashow, L S
                Bangera, M G
        (B) TITLE: U41818

(xi) SEQUENCE DESCRIPTION: SEQ ID NO:4:

```
GTCGACCCAG TAAAGGCAGA CAATGCATGG CTCGCTGCTG ATGCTTTGGG CGTGGTAAGG    60
AATCTGCAAC GGGTCCCCGT CAGTCTTGAG CAATCGACCG TTGCCTTTGT AATACCAGGC   120
CTGTTCCGTC TTGGCGGTGC ACAGTGTGAT CTCGCTGACC TGAACAGCCA AGTTGTCATC   180
GGGTTTGAGC GGCGGCCTGT ATTTCGCGCC TGTGGGCGAG AGCGGATAGG GCGTCGATGG   240
GAGGCTCCTG AGGTAGGATT CCCAATCCAT GTTCAGGCGA GCGCAGTGGC TCAGGGCTTC   300
ATAAAGGTTT CCCTGCGGTG ATCGTACTTC CAGGCTTTGC CCGGATTTGA AGTCGAATAC   360
ACCCAGCCCG CGCAGCGGCT GCGGCGAGTC CAATAGCATT ACGTAATGCG TCATCACTTA   420
TCCTCCAGCG TCAAGCGAGC GGGCAGGGGG CCGTAGTCCG CACGGTCATT GAAAACAGGG   480
CTGGCTTCCT TGAGCCGCAG GGACAGCAAC CCGCCCATCA AACTACCAGC CAGTGCCAGA   540
AACAGAATGG CGGTAAGCCC CCAGTTCACG GCGATGTACC CGGCGACCAC GGGCGCAACG   600
CCACCGCCCA GGATTTCTCC GCAACCCACC ACCAGGCCCG TAGCGGTGGC CAGTAAACTG   660
GGTGGCACTG ATTCGCTGGT CAGTGGGCCG ACGGTGATGC AGATCAGGCT GAAATTGATG   720
AAAGATAAAA AGAACAGCTG GAGGAACAGT AGCCACGGTA ACGGCGGGGA AATGATGAGC   780
AAGCCGACCA GTAGTGTGCT GATCAGGAAG CAGATGGAAA CGACAGGCTT GCGGCCCAGT   840
TGGTCAGACA AACCGGGAAT GACGAGCTGG CCGAAAAAAC CACCCAGGCC GATCGCGGAG   900
ATGATCATGG CCATGGAGAA ATTGCTCAGG TGCAAGACGT CTGTCAGGTA GCTGGGGAGC   960
AGGGCGCACA GGACGAATTG GCACGTCAGT ATGCATAGCA TCAAGGCAAT GTTGAGGCGC  1020
ACGTTGCCGC TGGACAGGGC TGTTCGCCAT TGGCTGCCGG AGGGTTCTAC GAGCGGCCTT  1080
GGATGGGGCG CCTGGCTCGG TTGGTAGGTT CGATACAGAT ACCAGGCCAC CAGCAGGCCC  1140
GGCAACGAGA TGATGGCGAA CACGGCGCGC CACGATCCGA ACATTTCAAA CAATACGCCC  1200
GCCAGCAGCG GCCCCAGGCA CAGGCCGATG ATGGGAAACA GTGCCTGCTG GATGCCCAGG  1260
TTGAGCCCGC GTCGGCACGG CTGCGAAAACT TCATCGGTGA CAATGATGCT GACCGGGGTG  1320
```

```
AAGGCGCCTT CGCAGATCCC CATCAAGGCG CGCAGGAGCA CCAGGCCCAT AAGGCTTGAG   1380

ATCAACGCAG ATGCGCCGGC CAGGAGCGAT ACCAAGGTAA TCGAAAGCAC AGCAGTTGC    1440

TTGGTGCCCA ATCGCCTGAT AGCAACGCCC ATGAAGAGGG CCGAGCCTCC CCAGGCAAAT   1500

GCCAGGATCG CCGATAACAG GCCCAGGTCC TGATAGTCCA GGGCCAGGTC ATGCATGATC   1560

ACCGGGAACA ACGGCATGAT AATGAATCGA TCAAGTCCTA CCAGCCCGAA GCTCAGCGAC   1620

AAAAGAACGA CCATGCGTCT TTCGTAGCCA CCCCAAGGTC GAGTGGCAAG ATACGTACTC   1680

TCCATGTTCT TCCCCTTCTT TCCTTAGCCC TTTCGACGTT TTCTCGAAAC GGGTGAACGC   1740

TTGTGTTCGA TACTCCTGTA GCCAGGGGCG GATCCGCCCC CGGCTTGGTG CGTGCAATGT   1800

GTTGGTCTGT CAGGCCACCC ACTTGCCCAC GGCCATTTCA GCTGTGAAGC CAGGGCCGAA   1860

GGCTGCCAGC ATGCCGGTCG CTCCATTGGC CGGCCCGCTG TCGAACTGGC GCTTGAGGAC   1920

GTCGAAGACC ACCACGCTGG CAATATTGCC GGCCTCGCTC AAGCTGTCGC GAGACTGCGC   1980

GACCCTGCCA GGTTCCAGAT CGAGCTGCAG CACCAGCTCA TCAAGAATTT TCGTCCACC    2040

GGTGTGGAAG ATGAAAAAGT CATTTTGAGC GCAATGTTGG TTGAAGGTCT CGAAGTTCAA   2100

TTCCTCCATC ATCGGGGCCA CGTCTTTAAT GGAGTTCATG ACGGCTTTGT CCAGGGTGAA   2160

GTGAAAGCCG CTGTCCTTGA CGTCATATTT AATGTAGTGC TCGCTGTCAG GCAGGAAATA   2220

AGAGCCGGTT TTGGCGATCT TGAATCCCGG CGCCTTATCG TCGGCGCGCA TTACGCAGGC   2280

CGAGACGGCA TCGCCGAACA GCGCTGCGGA TATGAACGCG TGCAACTTGG TGTCCTGTGG   2340

TTGATAGCAG AGTGACGAGA ACTCCAGCGA GACAATAAGG GCGTGGTTGT CTGGAGACAG   2400

GCTGGCAAAG TCGTTGGCTC GATTAATCGC CGCGGCGCCT GCCACGCATC CCAATTGAGC   2460

GATCGGCAAT TGTACGGTCG ACGTTCGCAG TCCCAAGTCA TTGATCAGGT GGGCTGTCAG   2520

CGATGGCATC ATGAACCCGG TGCAAGAGGT AACGGCGACC ATCCGGATGT CGTCCGTGGT   2580

CAAGCCCGCG TTTTCAATGG CCTGGCGCGC GGCGATTGAA GACATGCGGC GAGCCTCTCG   2640

CTCATACACG ATGCTGCGGT GGGTAAAGCC GGTATGCACC GCAAGTTCAT CGATGGGCAA   2700

GACCAGATAC CGTTCATTGA CTTGGGTGTT TTGAATCATC CGTTTAGCCA ATGCCATGCG   2760

CGGATGATCG TCATGCAACT GTTCCAAGTG ATCGATCATC TGTTGTTGGG TAATTTTGTA   2820

ATGCGGGAAA AGCAAGCTGG GTTTGCAAAG AGTAGACATG ACAAGTCCTC GGCTGAAAGC   2880

CAATAAAGAG TAGAAAACCA CGTTTAAGGC AATGGCAAAG CAGGACTCTG AAAAGCAGAA   2940

TCAAACAACG GGCCGGTTGG CCGGAAATAG CGACTGTTGT TATGGATGGC GCGGTATGCA   3000

GCAGTAACTT GTTTGTTATT TCGCCAATAC GAATTTATAA GCGTATTGCC ACGCCAGGTT   3060

GCTTTCCCGA ACGTGCTTGC GAATAACCAT TCGCACTGGT GCTCCAGTCA CGACTTGCCG   3120

GGATCGACG ACATCGACGA TTTCCGAGGC GATCACCAAG CCATCGTCCA GGCGCACCAT    3180

TGCCATGAAG CGCGGGACGG TTTCGCCATA TCCCATGGCC GCGAGAATGG GGTTTTCAGC   3240

ATGGGCGCTG ACCTGGATCG TGCCGGTGCG TGCGCAGCGA TACGGTTCCA CGTTCAATGA   3300

GTTGCATGCG CCGCAGACGG TGCGCCGTGG AAGAAGATT TCTTCGCAAT CCTGGCAGCG    3360

GCTGCCTTCG AGACGATATT TTCCGCCATG TTCGCGCCAT TCGCGCAACA TGCTGGCGGT   3420

GGTCATGCGG TGTATTTGTT CTGGGTAAAG GGACATGGTC GGCTCCTTAA TCGTTGGAAA   3480

GCACAATGAC GCTGTTATGC GCGGCGTAAC CGCCCAAGTT CTGCGAGACG CCAATGCGAG   3540

CGTCCTTGAC TTGGTTGTTG GACTCGCCGC GAAGTTGTCG GAACAGCTCG GTAATGTGCA   3600

GGATGCCGTC GCAACCAGAG GCGTGGCCGC GGCCAATATT GCCGCCATCG GTGTTTAATG   3660
```

```
GCAGTTGCCC GTCGAGGGCT ATGCCGCCTT CCAATACAAA GTCGCCTGCC TGGCCTGGAC    3720

CACATACGCC CATGGATTCC ATCTGAATCA ATCCGGCACC CAGCAAGTCG TAGACTTGGG    3780

CCACATCGAT ATCCTTGGCG GTGATGCCGG CTTTTTTGTA GGCGATTTCG GCGCAAGCAA    3840

TGGAGTTGGC GGAAACCGCC ATGCCGACGT CTTTTGGCAG GCCTGGATAT TTCAGGGTCG    3900

GGTTGTGATA GCGCGTCCCG AAATAATGGG ATACGCCGGT ATAGGCACAA CCACGGACGA    3960

ATACCGGTTG GGTCGTGTAG CGGTGCGCCA GGTGTTCGGC GACCAGGATG GCGCAACCGC    4020

TGGCTTCACC CCAGGCCAGC ATCGAGCCAC ATGCTTCGCT GTTCTTGAGG GTTTCAAGGG    4080

ATGGCACCGG CACGCCATAG CGGGTTGCCG TGGGCGTGTT GTGCGCATAG ATGCGCATTT    4140

GCCGACCAAA CGTTGCCAGG ACATCCGCTT CGCGTCCTGC ATAGCCAAAT TTTTCAAAAT    4200

ATTCGGCGGT TGCGAGGGCA AAGGCGTCGG TGTGCGAAAT GCCCAGGAAA TAATCGTACT    4260

CACATTCGGT ACTGGAGCCG ATGTATTCGG CATAGTTGAA GTGGTCGGTC ATTTTTTCAA    4320

AGCCACCACA CAGGACGATG TCGTACTCAC CCGAGGCGAC CATCTGATGG GCCATCTGAA    4380

AGGAAACCGA GCTGCTGGTG CAGTTGGCAG TGCTCATGAA CGTCGGGCA GGGCTGATGC    4440

CCAGGGCATC GGAAATAGTC GGGCCCAGGC CGCCGTATTC GGAAATACCT TCACCGTGAT    4500

ATCCATAAGC GACTGCCTGA AGTTCACGGG GATGCATCTT GATGGCGTTG AGCGCCTGAT    4560

AGGCGGACTC GACGATCATC TCCTTGAAGG TTTGACGGAC TCTGGAGCTG CCGGGTTTGG    4620

AAGTATAGGC AGCCGAAACG ATAGCAACGC GTCGTGCGCT CATTGGAAGT GCTCCTTGCT    4680

GGATGGTTGG GAATCAGAGG TAGGCTGTCA GGGCGTAGTC AGGCCGCAAG TATTTGAACT    4740

CGTACTTGAT CGACGTCCCG TAATCCACGT AATACTTGTC TTCCAGCAGC GTGCGCAGCG    4800

CAACGTTGGT CTTTTGGTAG GCTTCGATGG CATCGGTCAC TGTCAACGCA ATCGCATCGC    4860

TGCCCGCACC AAACCCGTAC GACACCAAGA GGATTTTTTC ACCCGGACGC GCTCGGTCCA    4920

GTACGCTCAC CAAGCCCAGC AACGGACTCG CGGCCCCCGC ATCACCGACA CTCTGGGCAT    4980

AAATGCCAGG TTCGATCTGC GCTTTGGTGA AGCCCAGGCC TTTGCCAAGA GAGAAGGGGG    5040

TCGAAACCAG GTTTTGCTGG AATACGACAT AGTCGAAATC GCTGGCCTGT ACATTCATCT    5100

TGGCCATCAA TCCCGACGCA GCACGATGGG TCTGGTCTTC AAGGCCAATG CTGTTCTTGT    5160

CGGAGCCCAG CCCCATTCCT GAGCGAATGT AGCGGTCTCC CTGGGGCGG ATGTTGTCAG    5220

CCACATCGGC GGCGCAAGAA AAGCTGGCAT CGAAATGCGC GATCACATTT TCAGTACCCA    5280

ACAACAGTGC GGCGGCTCCC GCTCCGGCGT AGGACTCGGT CAAGTCGCCG GGGCGGTGT    5340

TGCGGTTGAT CGTATCGGCG CCTATTGCCA GTGCATTGCC GGCCATGCCC GAGGCTACCA    5400

GGGCATAGGC GATCTGCAGG GCGCTGGTGC CTGATTTGCC GGCAAACTGT ACGTCCGCGC    5460

AGAAGGCGTC ATAACCGCAG CCGAGCATTT CCAGAATGAC CGCGGCCGAG GCGCGGGAGT    5520

CATATGGGTT GGTGCACGTA CCCAGGTACA GCGCTTCCAG GTCGCAAGAA GGGGCTTTGT    5580

CCAGCGCACG TTGAGCGGCC AGGACACTCA AGGTAATGAC GTCCTCATCG GGTTGGAGTA    5640

CAGCCCTTTC AACGACGCCC AGTTGGTTGG TGACCAGACT CAAGTCTGTG TTTTTCCAGA    5700

CGTGGATCAC GTCTTCCACT TTAAGGCGGC ACACCGGGAT GCCCGCGCCA TAGCTCACAA    5760

TTCCTACTTT ATTCACGTGT ACTTCCTCCA GATTCCTTTC TTCACCTGCC AGCGGATAGC    5820

CGTGACCGAT GCATGAAATA TTTAGAAACT ATCTAACGGT GCCCGCAAAG TGTCGTTGGC    5880

AGTCCTATGC CCGGAAATCG GGCTCCTCAA GGGGGAAAAC TACAGTTCCT TTGAGGGAGA    5940

ACGGGTTTAT TATCCTTCTA TTATTATGTA TGATACGAAA CGTGCCGTAT CGTTAAGGTC    6000

TTGTTAAAAA TTGATGACTA TTTATCGGGT TCTTCCTAT CTAGTGGCAA GTTCCGCTAT    6060
```

```
TGAGGTGTGC AGTTAAGCAG AAACTTAGAT CATAAAAACA TACAAAACGA AACGATCCGT    6120

TTCATTGCTT TTCGAGAGAA TCCTATACCT TGCGTCTCTT TTGTCAAGCG CCATATTGGA    6180

GATTTTGAAT TATGGCCCGT AAACCGTCTC GGAGCTCCAT GGCTCATTG AGGAGCCCAC     6240

ATACGCACAA AGCGATCATC ATCTCCGCTA TAGAAACACT CAAGGAGTGC GGTTATTCAG    6300

GGTTGAGTAT CGAGGCTGTG GCTCGCCGTG CCGGCGCGAG CAAGCCGACC ATCTATCGAT    6360

GGTGGGGTAA CAAGGCGGCT TTGATCGCCG AAGTCTACGA GAGCGAAAGC GAGCAGATTC    6420

GCAAGGAGCC TGATAAAGGA TCCTTCAAGG AGAACCTCAA TTTCCTGCTG CTCAATCTGT    6480

GGAAGGTCTG GAGAGAAACG ATTTGCGGGG AGGCGTTTCG GTGTGTCATC GCTGAAGCCC    6540

AGCTCGACCC CAGTACGCTG CCCAAGCTGA AGGATGAATT CATGGAGCGT CGTCGGGAAT    6600

TGCCGCGAAA GCTGGTGGAA AACGCCATCC AGCAAGGTGA GTTGCCCAAG GACACGTCCC    6660

GTGAGTTGTT GTTGGACATG ATCTTCGGAT TTTGCTGGTA CAGGCTGTTG ACTGAGCAAC    6720

TGGAAGTGGA GGGTGACATC AATGAATTCA CGACGCTTCT GTTGAACGGC GTGTTGCGTA    6780

CGACTTCGGC GGCGGAGTAA GGCGCCGCCG AAGCCTGTTC AAGGGTGAGG ATTGGCCTTA    6840

CGCCGCGCCG CTGAACTGTG CATGAAGGCC AGGCAGGATA CTGGCCAGGT GGTTGAACTC    6900

ACACAGATCA TGCACAGCAA ATTCATAAGC CAGGGTTTCC AGTTCGGCTT CCCCAAACCC    6960

GTTTTCCTTC AACAACTGCG CGGCGCGTTC GGCACCGGGA AAACGCAGCA TCGCTGGGTG    7020

GCTGCCCACC CAGTAACGGC TGGTCAGGTA CAAGCCTTCG GGGCATTCCT TGAACAAGTG    7080

CACCATGAGC GATATCGGCA CTTGCGGCTG ATCCGCCAGG CTCATCAAGG CGCTGACGCT    7140

GCCGTCTATT TTTGATTCGC GATACAGGTC CGCAGAGAAA CCCAGCTCGC ATGGATCC     7198
```

(2) INFORMATION FOR SEQ ID NO:5:

(i) SEQUENCE CHARACTERISTICS:
        (A) LENGTH: 349 amino acids
        (B) TYPE: amino acid
        (D) TOPOLOGY: linear (ii) MOLECULE TYPE: protein (xi) SEQUENCE DESCRIPTION: SEQ ID NO:5:

```
Met Ser Thr Leu Cys Lys Pro Ser Leu Leu Phe Pro His Tyr Lys Ile
 1               5                  10                  15

Thr Gln Gln Met Ile Asp His Leu Glu Gln Leu His Asp Asp His
            20                  25                  30

Pro Arg Met Ala Leu Ala Lys Arg Met Ile Gln Asn Thr Gln Val Asn
        35                  40                  45

Glu Arg Tyr Leu Val Leu Pro Ile Asp Glu Leu Ala Val His Thr Gly
    50                  55                  60

Phe Thr His Arg Ser Ile Val Tyr Glu Arg Glu Ala Arg Arg Met Ser
65                  70                  75                  80

Ser Ile Ala Ala Arg Gln Ala Ile Glu Asn Ala Gly Leu Thr Thr Asp
                85                  90                  95

Asp Ile Arg Met Val Ala Val Thr Ser Cys Thr Gly Phe Met Met Pro
            100                 105                 110

Ser Leu Thr Ala His Leu Ile Asn Asp Leu Gly Leu Arg Thr Ser Thr
        115                 120                 125

Val Gln Leu Pro Ile Ala Gln Leu Gly Cys Val Ala Gly Ala Ala Ala
    130                 135                 140

Ile Asn Arg Ala Asn Asp Phe Ala Ser Leu Ser Pro Asp Asn His Ala
```

-continued

```
145                 150                 155                 160
Leu Ile Val Ser Leu Glu Phe Ser Ser Leu Cys Tyr Gln Pro Gln Asp
                165                 170                 175
Thr Lys Leu His Ala Phe Ile Ser Ala Ala Leu Phe Gly Asp Ala Val
            180                 185                 190
Ser Ala Cys Val Met Arg Ala Asp Asp Lys Ala Pro Gly Phe Lys Ile
        195                 200                 205
Ala Lys Thr Gly Ser Tyr Phe Leu Pro Asp Ser Glu His Tyr Ile Lys
    210                 215                 220
Tyr Asp Val Lys Asp Ser Gly Phe His Phe Thr Leu Asp Lys Ala Val
225                 230                 235                 240
Met Asn Ser Ile Lys Asp Val Ala Pro Met Met Glu Glu Leu Asn Phe
                245                 250                 255
Glu Thr Phe Asn Gln His Cys Ala Gln Asn Asp Phe Phe Ile Phe His
            260                 265                 270
Thr Gly Gly Arg Lys Ile Leu Asp Glu Leu Val Leu Gln Leu Asp Leu
        275                 280                 285
Glu Pro Gly Arg Val Ala Gln Ser Arg Asp Ser Leu Ser Glu Ala Gly
    290                 295                 300
Asn Ile Ala Ser Val Val Val Phe Asp Val Leu Lys Arg Gln Phe Asp
305                 310                 315                 320
Ser Gly Pro Ala Asn Gly Ala Thr Gly Met Leu Ala Ala Phe Gly Pro
                325                 330                 335
Gly Phe Thr Ala Glu Met Ala Val Gly Lys Trp Val Ala
                340                 345
```